United States Patent
Wang

(10) Patent No.: US 7,604,346 B2
(45) Date of Patent: Oct. 20, 2009

(54) PROTECTIVE GLASSES ASSEMBLY

(75) Inventor: Ching-Hsiang Wang, Tainan (TW)

(73) Assignee: Day Sun Industrial Corp., Tainan (TW)

( * ) Notice: Subject to any disclaimer, the term of this patent is extended or adjusted under 35 U.S.C. 154(b) by 203 days.

(21) Appl. No.: 11/765,901

(22) Filed: Jun. 20, 2007

(65) Prior Publication Data

US 2008/0316421 A1    Dec. 25, 2008

Related U.S. Application Data

(63) Continuation-in-part of application No. 11/683,700, filed on Mar. 8, 2007, now Pat. No. 7,322,051.

(51) Int. Cl.
*G02C 1/00* (2006.01)
*A61F 9/02* (2006.01)

(52) U.S. Cl. .............................. 351/43; 351/156; 2/441; 2/452

(58) Field of Classification Search ................... 351/43, 351/156, 41, 158; 2/441, 452, 448, 430, 2/428, 431
See application file for complete search history.

(56) References Cited

U.S. PATENT DOCUMENTS

| 5,617,588 | A | * | 4/1997 | Canavan et al. | ................. | 2/428 |
| 6,149,268 | A | * | 11/2000 | Hall et al. | ...................... | 351/62 |
| 7,003,811 | B2 | | 2/2006 | Canavan | ......................... | 2/448 |
| 7,162,750 | B2 | | 1/2007 | Canavan | ......................... | 2/448 |
| 7,322,051 | B1 | | 1/2008 | Wang | ............................ | 2/448 |

\* cited by examiner

*Primary Examiner*—Hung X Dang
(74) *Attorney, Agent, or Firm*—Alan Kamrath; Kamrath & Associates PA

(57) ABSTRACT

A protective glasses assembly has an integrally formed designed lens, a frame made of a soft material and fitted in with the designed lens and a band. A plurality of spaced apart male portions extend rearward from edges of the designed lens for being inserted into sockets of corresponding covering elements extending forward from edges of the frame, and a number of air-passing grooves are located on upper and lower edges of the frame. The designed lens has engaging blocks respectively formed on left and right sides for engaging with boundary holes of connector members connected with both ends of the band, and through holes for receiving inner inserting sections of the connector members. Thereby the designed lens and the frame can be assembled promptly and kept in a stable position.

1 Claim, 5 Drawing Sheets

PROTECTIVE GLASSES ASSEMBLY

CROSS REFERENCE

The present application is a continuation-in-part of U.S. application Ser. No. 11/683,700 filed Mar. 8, 2007, now U.S. Pat. No. 7,322,051.

FIELD OF THE INVENTION

The present invention is related to a protective glasses assembly; more particularly related to an assembly of integrally formed design lens and a soft frame as attached with a band having two ends connected with connector members, such that stable positioning and convenient and prompt attachment and detachment can be achieved when replacing elements.

BACKGROUND OF THE INVENTION

Conventional designs of eyeglass assembly combining designed lens with a soft frame typically utilizes two elements that are first engaged together directly to be attached with a band for stably mounting on a human head to construct an eyeglass assembly for users' selection as needed.

SUMMARY OF THE INVENTION

The present invention provides an alternate design combing a conventional integrally formed lens with a frame and a band so as to achieve stable positioning and prompt and convenient assembling if component replacement is required.

One object of the present invention is to provide a plurality of spaced apart male portions extending rearward from edges of the designed lens for being inserted into sockets of corresponding covering elements extending forward from edges of the frame, and more than one protrusion extending rearward from a nose supporting portion of the designed lens for being received in more than one groove on a front surface of a nose supporting portion of the frame. Thereby the protective glasses assembly can be promptly and easily detached if component replacement is required.

Another object of the present invention is to provide engaging blocks respectively formed on left and right sides of the designed lens and connector members connected with both ends of the band. Each of the connector members has an inner inserting section and a boundary hole. Each connector member is pushed along an outside of each engaging block of the designed lens with the inserting section of the connector member being inserted into a through hole on each end of the frame until the engaging block of the designed lens being completely limited by the boundary hole of the connector member. Thereby the designed lens and the frame can be assembled promptly and kept in a stable position.

Yet another object of the present invention is to provide a number of air-passing grooves located on upper and lower edges of the frame so as to allow air to flow there through for venting purpose so that the protective glasses assembly is comfortable to wear.

DETAILED DESCRIPTION OF THE EMBODIMENTS

Figure 2:
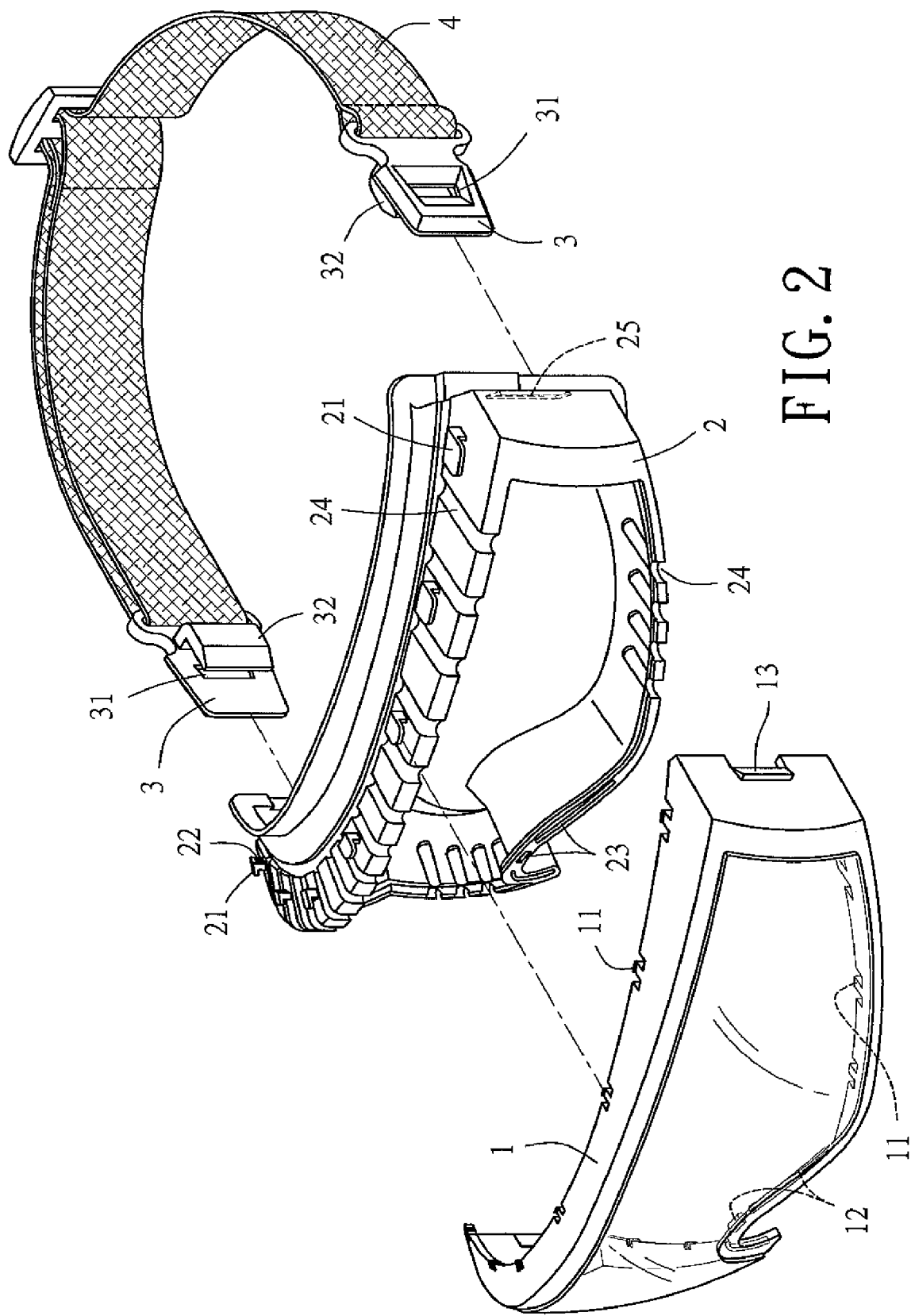
FIG. 2 is an exploded perspective view of the protective glasses assembly in accordance with the present invention.

Referring to FIG. 2, a protective glasses assembly in accordance with the present invention is shown. The assembly includes an integrally formed designed lens 1, a frame 2 made of soft material and fitted into the designed lens 1, and a band 4 having two ends respectively connected with connector members 3.

The designed lens 1 has an inner surface formed with a plurality of spaced apart male portions 11 extending rearward from edges, more than one protrusion 12 extending rearward from a nose supporting portion and engaging blocks 13 formed on left and right sides.

Figure 3:
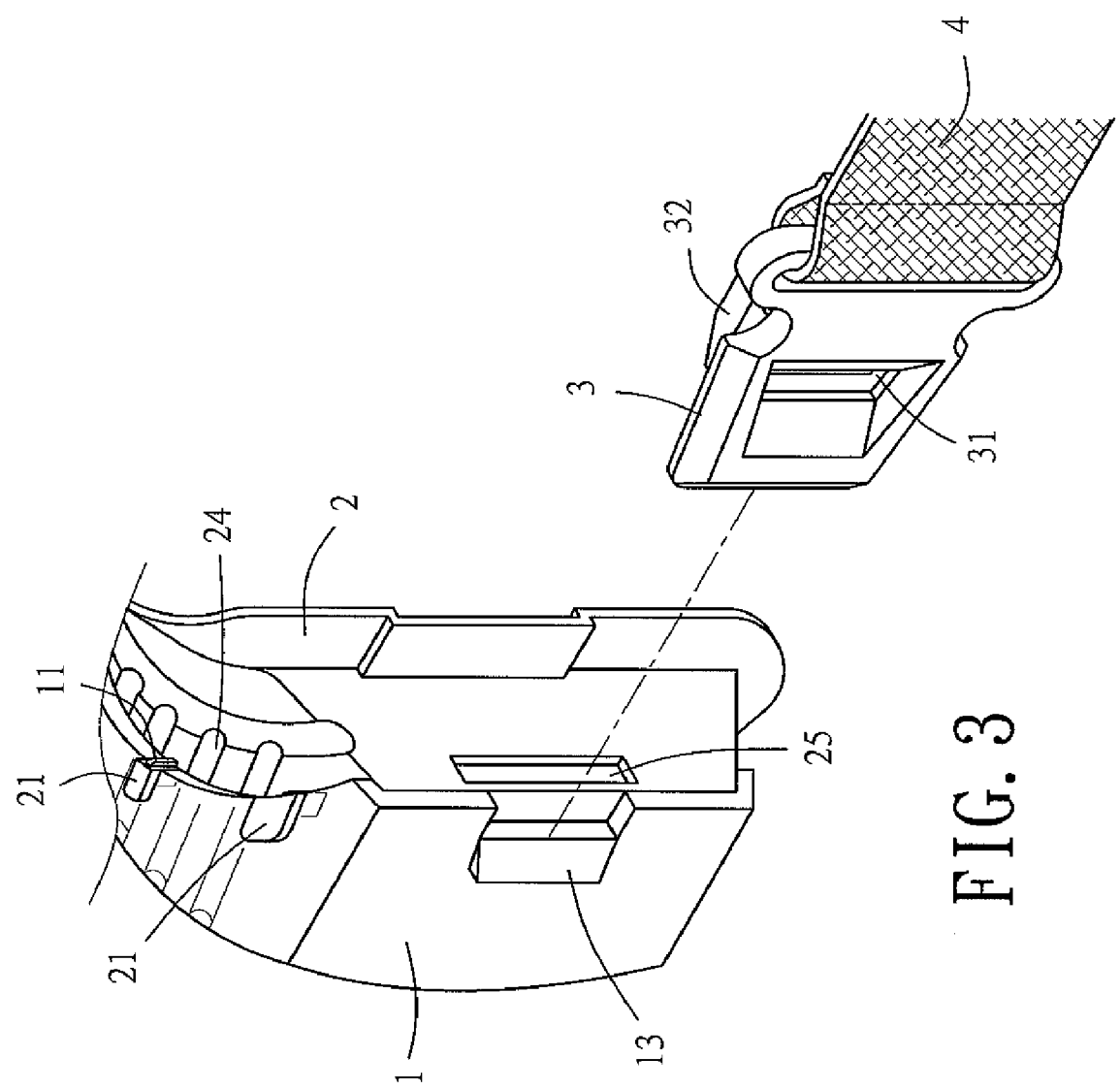
FIG. 3 is a schematic view before a band is engaged with the assembly of a designed lens and a frame.

The frame 2 is made of a soft material and shaped to shape of the designed lenses 1. A plurality of covering elements 21 extend forward from edges of the frame 2 and are spaced at intervals corresponding to the spaced intervals of the male portions 11. Every covering element 21 further has a socket for receiving the corresponding male potion 11. The frame 2 further has more than one groove 23 provided on a front surface of a nose supporting portion, at the position corresponding to the protrusion 11. A number of air-passing grooves 24 are provided at spaced intervals along the upper and lower edges of the frame 2. The left and right sides of the frame 2 are respectively provided with through holes 25, as shown in FIGS. 2 and 3.

Each connector member 3 of the band 4 has an inner inserting section 32 and a boundary hole 31.

Figure 1:
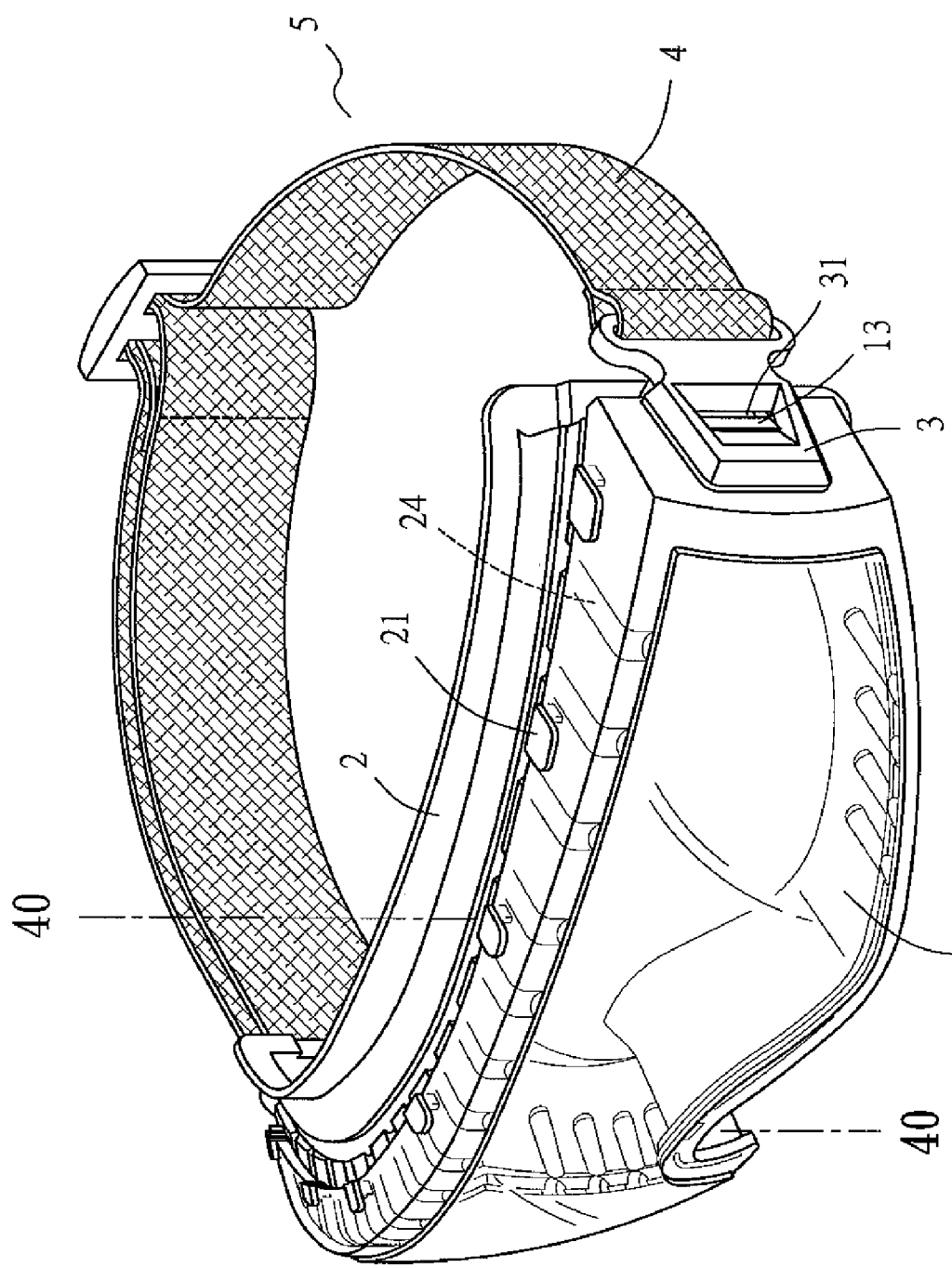
FIG. 1 is a perspective view of a protective glasses assembly in accordance with the present invention.
Figure 4:
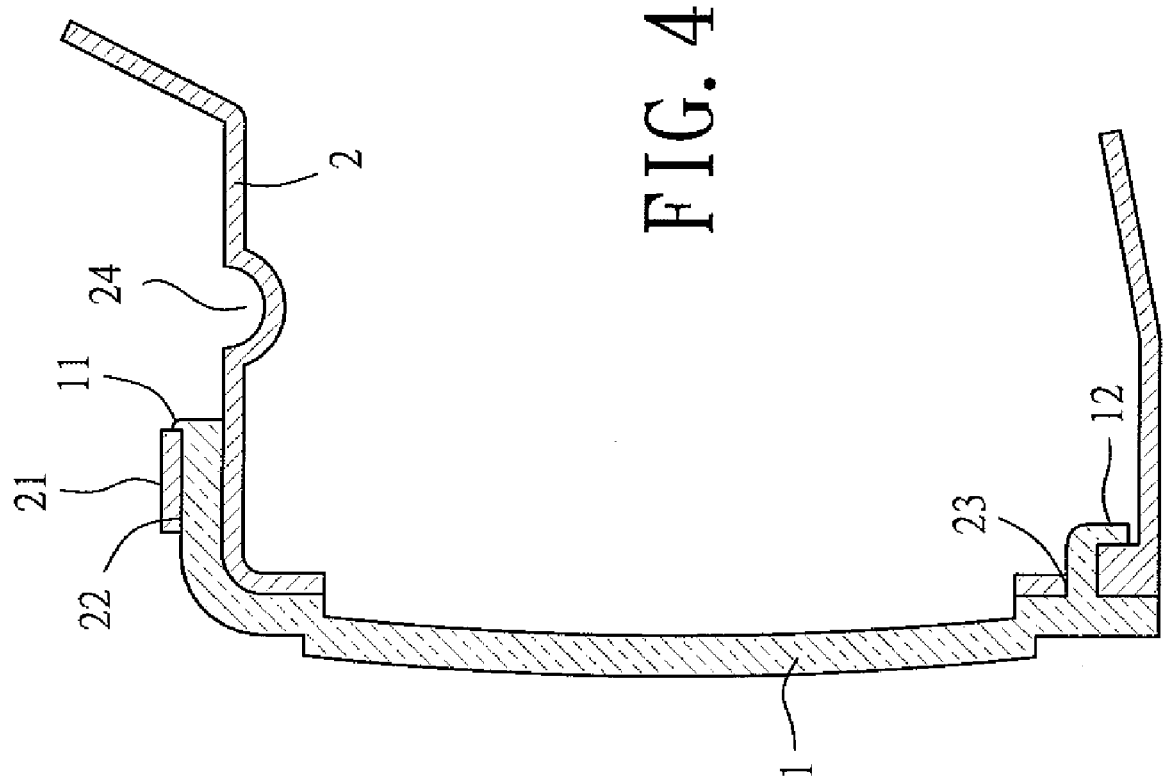
FIG. 4 is a detailed cross-sectional view taken along line 40-40 of FIG. 1.
Figure 5:
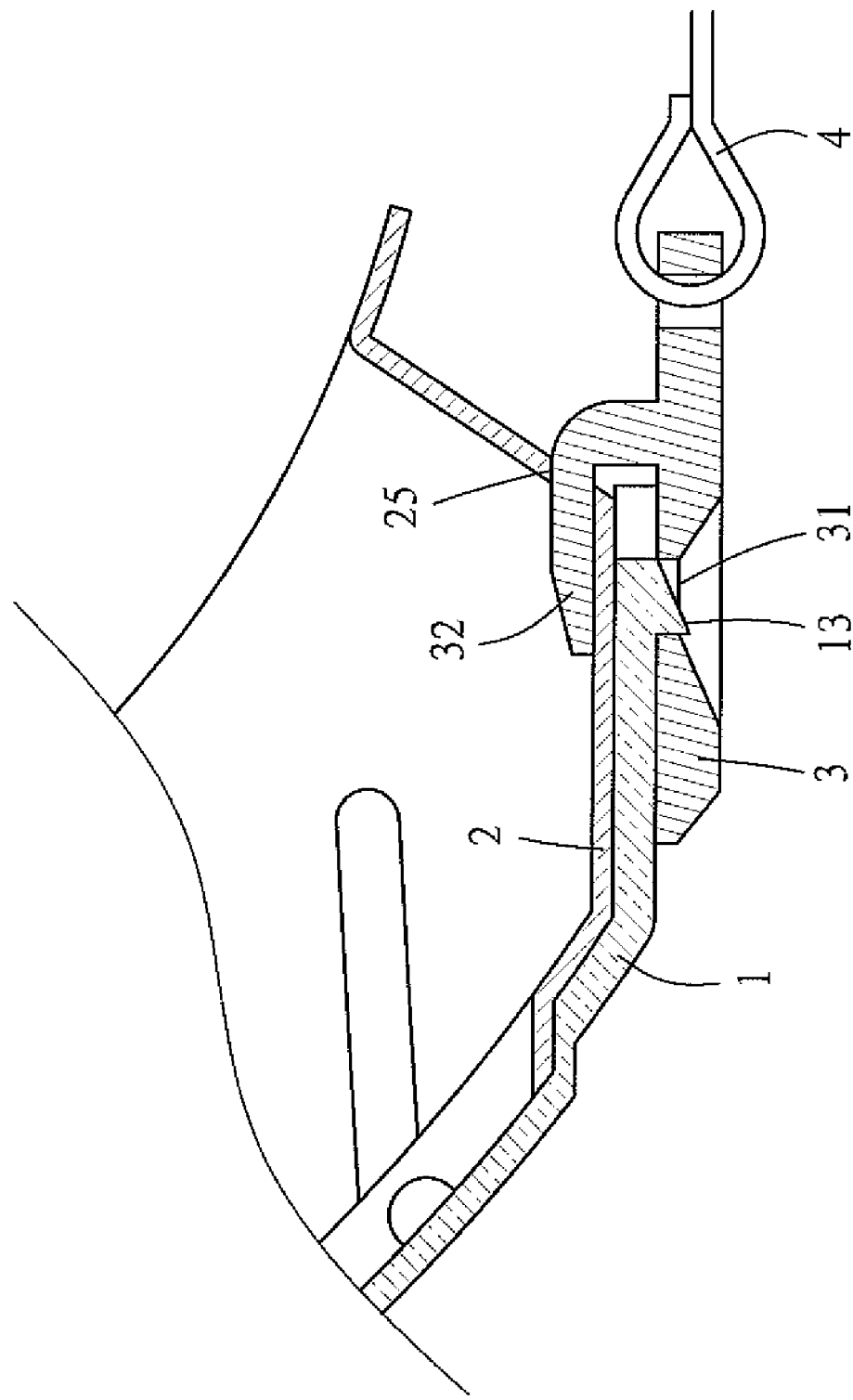
FIG. 5 is a detailed cross-sectional view of connector members of the band attached with the designed lens and the frame in accordance with the present invention.

FIG. 4 shows assembling operation of the protective glasses assembly 5. Each of the rearward-extending male portions 11 located at spaced intervals along the edges of the designed lens 1 is inserted through the socket 22 of the corresponding covering element 21 while the more than one protrusion 12 on the nose supporting portion of the designed lens 1 being accommodated in the corresponding groove 23 on the nose supporting portion of the frame 2. The air-passing grooves 24 located on the upper and lower edges of the frame 2 fitted in the designed lens 1 allow air to flow there through for venting purpose. Then each connector member 3 at each end of the band 4 are pushed along an outside of the engaging block 13 of the designed lens 1, as shown in FIG. 5, so that the inserting section 32 of the connector member 3 is inserted into the through hole 25 on each end of the frame 2 until the engaging block 13 of the designed lens 1 completely enters the boundary hole 31 of the connector member 3; as a result, the connector members 3 at both ends of the band 4 are stably engaged with the designed lens 1 combined with the frame 2, as shown in FIG. 1.

The protective glasses assembly in accordance with the present invention, as described above, has the following advantages:

1. The designed lens and the frame can be quickly assembled and stably positioned by means of clicking.

2. The number of air-passing grooves located on the upper and lower edges of the frame allow air to flow there through for venting purpose so that the protective glasses assembly is comfortable to wear.

3. The connector members at both ends of the band, for attaching the band with the assembly of the lens and the frame, are stably positioned after being attached and can be detached promptly as needed.

4. The elements of the protective glasses assembly can be promptly and easily detached if replacement is required.

What is claimed is:

1. A protective glasses assembly, comprising an integrally formed designed lens, a frame made of a soft material and fitted in with the designed lens and a band; wherein the designed lens has engaging blocks respectively formed on left and right sides and both ends of the band are connected with connector members each having an inner inserting section and a boundary hole, and each connector member is pushed along an outside of each engaging block of the designed lens with the inserting section of the connector member being inserted into a through hole on each end of the frame until the engaging block of the designed lens being completely limited by the boundary hole of the connector member; thereby the designed lens and the frame can be assembled promptly and kept in a stable position.

* * * * *